United States Patent
Wu et al.

(10) Patent No.: US 10,557,177 B2
(45) Date of Patent: Feb. 11, 2020

(54) METHODS FOR ASSESSING TOXICITY

(71) Applicant: Nanjing University, Nanjing (CN)

(72) Inventors: Bing Wu, Nanjing (CN); Yue Yu, Nanjing (CN); Huimei Chen, Nanjing (CN); Su Liu, Nanjing (CN); Xuxiang Zhang, Nanjing (CN); Hongqiang Ren, Nanjing (CN)

(73) Assignee: NANJING UNIVERSITY, Nanjing (CN)

( * ) Notice: Subject to any disclaimer, the term of this patent is extended or adjusted under 35 U.S.C. 154(b) by 66 days.

(21) Appl. No.: 15/869,016

(22) Filed: Jan. 11, 2018

(65) Prior Publication Data

US 2018/0135139 A1 May 17, 2018

(30) Foreign Application Priority Data

Jul. 25, 2017 (CN) .......................... 2017 1 0616052

(51) Int. Cl.
| | | |
|---|---|---|
| *C12Q 1/6897* | (2018.01) | |
| *C12N 15/68* | (2006.01) | |
| *C12Q 1/02* | (2006.01) | |
| *C12Q 1/06* | (2006.01) | |
| *C12Q 1/42* | (2006.01) | |
| *G01N 33/18* | (2006.01) | |
| *C12N 15/85* | (2006.01) | |

(52) U.S. Cl.
CPC .......... *C12Q 1/6897* (2013.01); *C12N 15/68* (2013.01); *C12Q 1/025* (2013.01); *C12Q 1/06* (2013.01); *C12Q 1/42* (2013.01); *G01N 33/1866* (2013.01); *C12N 2015/859* (2013.01)

(58) Field of Classification Search
None
See application file for complete search history.

(56) References Cited

U.S. PATENT DOCUMENTS

| | | | | |
|---|---|---|---|---|
| 2004/0101971 | A1* | 5/2004 | Voice ........................ | G01N 1/40 436/174 |
| 2005/0251872 | A1* | 11/2005 | Bear ................... | A01K 67/0275 800/8 |
| 2006/0183189 | A1* | 8/2006 | Fussenegger ...... | A01K 67/0271 435/69.1 |
| 2009/0061022 | A1* | 3/2009 | Lee ......................... | A61K 31/00 424/623 |
| 2010/0304384 | A1* | 12/2010 | Valdivieso mate .......................... | C07K 14/4702 435/6.13 |
| 2016/0327557 | A1* | 11/2016 | Haught ................ | G01N 33/579 |

OTHER PUBLICATIONS

'Secreted Alkaline Phosphatase Reporter Gene Assay Kit' Instructional manual; Cayman Chemical, Ann Arbor, MI, USA, Sep. 6, 2016 (Year: 2016).*

* cited by examiner

*Primary Examiner* — Addison D Ault
(74) *Attorney, Agent, or Firm* — Matthias Scholl P.C.; Matthias Scholl (57) ABSTRACT

A method for characterizing toxicity of toxic pollutants and a method for characterizing comprehensive toxicity of water bodies. The methods include constructing a reporter gene cell line expressing CHOP gene associated with endoplasmic reticulum stress.

5 Claims, 4 Drawing Sheets

METHODS FOR ASSESSING TOXICITY

CROSS-REFERENCE TO RELATED APPLICATIONS

Pursuant to 35 U.S.C. § 119 and the Paris Convention Treaty, this application claims foreign priority to Chinese Patent Application No. 201710616052.5 filed Jul. 25, 2017, the contents of which are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

Field of the Invention

The present disclosure relates to the field of detection of cytotoxicity caused by contaminants, and more particularly to the use of a reporter gene cell line based on endoplasmic reticulum stress in characterizing toxicity of pollutants.

Description of the Related Art

Reporter gene assay is widely used in toxicity evaluation because of its sensitivity, rapidity, and reproducibility. Researches have shown that the reporter gene method can significantly lower the toxicity detection limit, improve the sensitivity, and shorten the response time. The current research based on reporter gene is mainly to monitor the specific target substances, such as DNA damaging substances, endocrine disruptors, dioxins, and other substances through the specific combination of inducible gene and reporter gene. However, different pollutants have different mechanisms of toxicity. Previous studies have shown that endoplasmic reticulum stress and damage is one of the common effects of pollutant toxicity. Therefore, the construction of a reporter gene cell line that can indicate the early stage of endoplasmic reticulum stress and damage can be more sensitive to detect the early contaminant toxicity.

Water pollution is a serious threat to human health. The existing analysis methods for water quality are mainly based on physical and chemical indicators (COD, BOD, ammonia nitrogen, total nitrogen, total phosphorus, etc.) and biological testing (bioindicator method, acute toxicity assessing based on luminous bacteria, toxicity testing using large flea, etc.) combination. Human cytotoxicity test, compared with traditional toxicity testing methods, can more directly reflect the impact of polluted water on human health but with limited sensitivity. Common methods used to assess cell viability, oxidative damage, genetic damage, and other toxic damage at cellular level are time-consuming and complex, and each can only analyze a specific class of toxic effects caused by the environmental pollutants on cells or organisms. Therefore, it is urgent to establish a simple and easy toxicity assessing method to evaluate the comprehensive toxicity of water. In recent years, reporter gene method based on the regulation of cell stress gene promoters have become one of the most promising methods of toxicity assessment, reported gene assay is widely used in toxicity evaluation because of its sensitive, rapid and reproducible characteristics. Studies have shown that the reporter gene method can significantly reduce the lowest detectable amount of toxin on the toxicity detection, improve the sensitivity and shorten the response time. The current research based on reporter gene is mainly to detect the presence of endocrine disruptors by combinations of specifically targeting gene and reporter gene, and by monitoring specific target substances. For example, the combination of endocrine disruptor receptor gene and reporter gene is used for monitoring the existence of endocrine disruptors; the combination of Gadd153 and the reporter gene can monitor DNA damage in the environment; the combination of HSE and reporter gene can monitor heavy metals. However, since water bodies comprise pollutants having different mechanisms of toxicity, a simple monitoring of certain types of specific target substances in water cannot fully characterize the comprehensive toxicity of water bodies and indicate the early toxic damage caused by the pollutants. Therefore, the construction of a reporter gene cell line that can indicate early cell stress and injury, be sensitive to detect the early toxic effects of pollutants, and characterize the combined toxicity of water will be more sensitive for assessing water safety.

SUMMARY OF THE INVENTION

It is one objective of the present disclosure to provide a method for characterizing toxicity of toxic pollutants.

It is another objective of the present disclosure to provide a method for characterizing comprehensive toxicity of water bodies.

To achieve the above objective, in accordance with one embodiment of the present disclosure, there is provided a method for characterizing toxicity of toxic pollutants, the method comprising constructing a reporter gene cell line based on endoplasmic reticulum stress.

In accordance with another embodiment of the invention, there is provided a method for characterizing comprehensive toxicity of water bodies, the method comprising using a reporter gene cell line based on endoplasmic reticulum stress.

The reporter gene cell line of the present disclosure can not only indicate the stress effect of the endoplasmic reticulum in the early stage of toxic damage, characterize the toxic effects of toxic pollutants and toxic damage, but also characterize the comprehensive toxicity of water.

Using arsenic as a typical toxic pollutant, dilution concentration gradient: 0, 0.05, 0.1, 0.15, 0.2, 0.5, 1 μmol/L. Seven groups of parallel comparison test were carried out. Transfected Hela cells were exposed to different concentrations of arsenic for 24 h. The supernatant of Hela cells was incubated at 65° C. for 30 min, and the SEAP activity of Hela cells was detected by a SEAP Reporter Gene Assay kit comprising a cell-based alkaline phosphatase standard and a SEAP substrate (SEAP activity has the effect of indicating luminescence, easy to monitor). The cell-based alkaline phosphatase standard and the samples were added to a 96-well white plate at 10 μL per well. Each well was added with 50 μL the SEAP substrate, and the chemiluminescence was detected at room temperature after incubating the 96-well plate for 10-30 min. The higher the toxicity, the higher the activity of SEAP in Hela cells, the stronger the chemiluminescence.

Application of a reporter gene cell line based on endoplasmic reticulum stress in characterizing the comprehensive toxicity of water bodies.

Water samples in chemical industrial parks are used as poisonous substances. 5 L water samples were concentrated by solid phase extraction and diluted with 2% DMSO to 1 mL. The concentrated samples were diluted to four dilutions respectively comprising by volume 0, 0.02%, 1% and 2% of the concentrated water samples, corresponding to 0, 1, 50, and 100 times the original concentrations of the water samples. The transfected Hela cells were exposed to different concentrations of water samples for 24 h, and the parallel comparison test was carried out. The supernatant of Hela cells was incubated at 65° C. for 30 min, and the SEAP activity of Hela cells was detected by a SEAP Reporter Gene Assay kit comprising a cell-based alkaline phosphatase standard and a SEAP substrate (SEAP activity has the effect of indicating luminescence, easy to monitor). The cell-based alkaline phosphatase standard and the samples were added to the 96-well white plate at 10 μL per well. Each well was added with 50 μL the SEAP substrate, and the chemiluminescence was detected at room temperature after incubating the 96-well white plate for 10-30 min. The higher the toxicity, the higher the activity of SEAP in Hela cells, the stronger the chemiluminescence.

Construction of reporter gene cell lines based on endoplasmic reticulum stress: The CHOP promoter was constructed by using the CHOP gene associated with the endoplasmic reticulum stress as a specific inducing gene. The CHOP promoter was ligated with the SEAP gene for easy detection to construct the lentivirus CHOP-SEAP plasmid vector. Finally, CHOP-SEAP plasmids were transfected into Hela cells to obtain the desired detection cell lines.

Among them, the endoplasmic reticulum stress will induce three signal pathways, and each signal pathway will induce CHOP gene expression, which means that endoplasmic reticulum stress will induce CHOP gene expression.

The above-mentioned method for constructing a cell line based on endoplasmic reticulum stress, comprising the steps of:

Step 1, construct the lentivirus CHOP-SEAP plasmid vector: The pHBLV-CMVIE-ZsGreen-Puro vector was cleaved with EcoRI and XhoI enzymes and extracted by gel electrophoresis; primers were designed according to SEAP gene and CHOP gene sequences and PCR amplification was performed. The amplified fragments were ligated with the vector and then transformed into DH5a competent cells. After transformation, strains were selected from the plate and shaken for 14 h at 250 rpm and 37° C. PCR identification was performed with the strains to obtain positive clonal bacterial liquid which is sent for sequencing.

Step 2, Lentivirus CHOP-SEAP Plasmid Vector Extraction: The lentiviral CHOP-SEAP plasmid vector was extracted from the positive clones obtained in step 1, and the extraction was carried out according to the instructions of the plasmid extraction and purification kit. When the lentivirus CHOP-SEAP plasmid vector concentration was more than 1 μg/μL, and the value of A260/280 was between 1.7 and 1.8, the virus can be packed.

Step 3, lentivirus CHOP-SEAP vector packaging: 293T cells were plated for transfection, and incubated after the transfection at 37° C. in an incubator containing 5% $CO_2$. When the cell confluence rate reached 70-80%, the liposomes were transfected, and the transfection system of each dish 100 mm was as follows:

| | |
|---|---|
| pSPAX2 | 10 μg |
| pMD2G | 5 μg |
| CHOP-SEAP plasmid | 10 μg |
| LipofiterTM dosage | 75 μL; |

The medium was replaced with fresh complete medium containing 10% fetal bovine serum after transfection. The virus supernatant was collected twice at 48 h and 72 h after transfection. The collected supernatant was centrifuged in a 50 mL centrifuge tube at 4° C. and 2000×g for 10 min to remove cell debris. And then the supernatant of the collected virus solution was placed in an ultracentrifuge tube and centrifuged at 82700×g for 120 min at 4° C. Finally, the lentivirus's ultra-centrifugal solution was dispensed into a sterile treated virus tube, packed and labeled well and preserved at −80° C.

Step 4, Construction of stable transfected cell line: Cells were cultured in 10 cm large dish. After the bottom of the large dish was covered with the cells, the cells were digested with trypsin and the cells density was diluted to $3.0 \times 10^5$ cells/mL. The diluted cell fluid was seeded on a six-well plate and the inoculum volume was 2 mL so that the fusion rate of cells cultured for the next day (24 h) was about 60% which is conducive for infection. Cells were infected and the original medium was discarded. 2 mL of DMEM containing 5% FBS, 1% double antibody and an appropriate amount of virus suspension was added to each well. 24 h after infection, the virus infection solution was discarded and medium was replaced with fresh complete medium. After the cells were infected with the virus, the cells were transferred to 10 cm large dish when the cell aggregation rate reached 90%.

Step 5, Screening of stable transfected cell line: Due to the puromycin resistance gene of virus's carrier, the cells infected with the virus will have puromycin resistance. According to this feature, repeated treatment of virus-infected cells with multiple use of puromycin can be used to screen out cells that have been successfully infected with the virus, followed by expanded incubation and cryopreservation.

Compared with other prior art, the technical proposal of the invention has the following advantages:

The detection cell line constructed by the invention can indicate early cytotoxic injury on the one hand, which can characterize the early toxicity of poisonous pollutants, greatly improve the detection sensitivity of cytotoxic damage and apply to most poisonous pollutants; The detection cell line constructed by the invention can not only indicate the early endoplasmic reticulum stress effect of poison contaminants, characterize the toxic effects of toxic pollutants, but also characterize the comprehensive toxicity of water bodies; The SEAP gene of the reporter gene selected from the constructed cell lines has the advantages of easy detection and dynamic monitoring.

DETAILED DESCRIPTION OF THE EMBODIMENTS

The technical solution of the present disclosure will be described further below with reference to the accompanying drawings.

Example 1

Step 1, construct the lentivirus CHOP-SEAP plasmid vector: The pHBLV-CMVIE-ZsGreen-Puro vector was cleaved with EcoRI and XhoI enzymes, extracted by gel electrophoresis; primers were designed according to SEAP gene and CHOP gene sequences and PCR amplification was performed. The amplified fragments were ligated with the vector and then transformed into DH5a competent cells. After transformation, bacterial strains were selected from the plate and shaken at 250 rpm and 37° C. PCR identification of the bacterial strains was performed to obtain positive clonal bacterial liquid. The positive clonal bacterial liquid was sent for sequencing.

Step 2, Lentivirus CHOP-SEAP Plasmid Vector Extraction: The lentiviral CHOP-SEAP plasmid vector was extracted from the positive clonal bacterial liquid obtained in step 1, and the extraction was carried out according to the instructions of the plasmid extraction and purification kit. When the lentivirus CHOP-SEAP plasmid vector concentration was more than 1 μg/μL, and the value of A260/280 is between 1.7 and 1.8, the virus can be packed.

Step 3, lentivirus CHOP-SEAP vector packaging: 293T cells were plated for transfection. The 293T cells were incubated at 37° C. in an incubator containing 5% $CO_2$. When the cell confluence rate reached 70-80%, the liposomes were transfected, and the transfection system of each dish 100 mm was as follows:

| | |
|---|---|
| pSPAX2 | 10 μg |
| pMD2G | 5 μg |
| CHOP-SEAP plasmid | 10 μg |
| LipofiterTM dosage | 75 μL; |

The medium was replaced with the fresh complete medium containing 10% fetal bovine serum after transfection. The virus supernatant was collected twice at 48 h and 72 h after transfection. The collected supernatant was centrifuged in a 50 mL centrifuge tube at 4° C. and 2000×g for 10 min to remove cell debris. And then the supernatant of the collected virus solution was placed in an ultracentrifuge tube and centrifuged at 82700×g for 120 min at 4° C. Finally, the lentivirus's ultra-centrifugal solution was dispensed into a sterile treated virus tube, packed and labeled well and preserved at −80° C.

Step 4, Construction of stable transfected cell line: Cells were cultured in 10 cm large dish. When the bottom of the culture dish was covered with the cells, the cells were digested with trypsin and the cells density was diluted to $3.0×10^5$ cells/mL. The diluted cell fluid was seeded on a six-well plate and the inoculum volume was 2 mL so that the fusion rate of cells cultured for the next day (24 h) was about 60% which is conducive for infection. Cells were infected and the original medium was discarded. 2 mL of DMEM containing 5% FBS, 1% double antibody and an appropriate amount of virus suspension was added to each well. 24 h after infection, the virus infection solution was discarded, and the medium was replaced with fresh complete medium. After the cells were infected with the virus, the cells were transferred to 10 cm large dish when the cell aggregation rate reached 90%.

Step 5, Screening of stable transfected cell line: Due to the puromycin resistance gene of virus's carrier, the cells infected with the virus will have puromycin resistance. According to this feature, repeated treatment of virus-infected cells with multiple use of puromycin can be used to screen out cells that have been successfully infected with the virus, followed by expanded culture and cryopreservation.

Using arsenic as a typical toxic pollutant, dilution concentration gradient: 0, 0.05, 0.1, 0.15, 0.2, 0.5, 1 μmol/L. seven groups of parallel comparison tests were carried out. The transfected Hela cells were exposed to different concentrations of arsenic for 24 h. The supernatant of Hela cells was incubated at 65° C. for 30 min, and the SEAP activity of Hela cells was detected by a SEAP Reporter Gene Assay kit comprising a cell-based alkaline phosphatase standard and a SEAP substrate (SEAP activity has the effect of indicating luminescence, easy to monitor). According to the SEAP Reporter Gene Assay kit protocol, the cell-based alkaline phosphatase standard and the sample were added to the 96-well white plate at 10 μL per well. Each well was added with 50 μL the SEAP substrate and the 96-well white plate was incubated for 10-30 min. The chemiluminescence was detected at room temperature. The experimental results are shown in FIG. 1.

Figure 1:
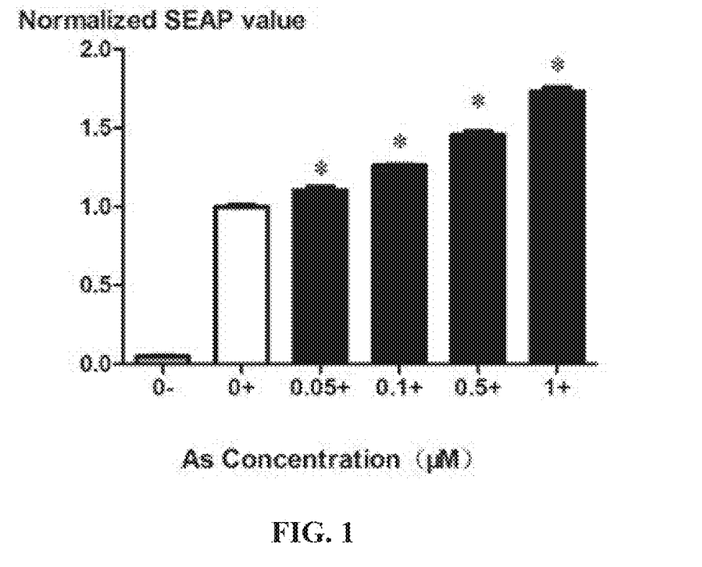
FIG. 1 shows the activity of SEAP after exposure to arsenic (μmol/L) in Example 1, where 0− represents the SEAP activity of untransformed and untransfected Hela cells; 0+ indicates the SEAP activity of transformed and untransfected Hela cells.

As can be seen from FIG. 1, there was a significant difference between the different exposure groups and the control group ($p<0.05$). The exposure group with an arsenic concentration of 0.05 μmol/L demonstrates a significant difference from the control group, indicating that the cell lines constructed by the method can characterize early cell damage, and the results show a dose-effect relationship.

Example 2

Using water samples as poisons, dilution concentration gradient: 0, 0.02%, 1% and 2% (The dilution concentrations are 0, 1, 50, and 100 times the original concentrations, respectively). Parallel comparison test was carried out. The transfected Hela cells were exposed to different concentrations of water samples for 24 h. The supernatant of Hela cells was incubated at 65° C. for 30 min, and the SEAP activity of Hela cells was detected by a SEAP Reporter Gene Assay kit comprising a cell-based alkaline phosphatase standard and a SEAP substrate (SEAP activity has the effect of indicating luminescence, easy to monitor). According to the SEAP Reporter Gene Assay kit protocol, the cell-based alkaline phosphatase standard and the sample were added to the 96-well white plate at 10 μL per well. Each well was added with 50 μL the SEAP substrate and the 96-well white plate was incubated for 10-30 min. The chemiluminescence was detected at room temperature. The experimental results are shown in FIG. 5.

Figure 5:
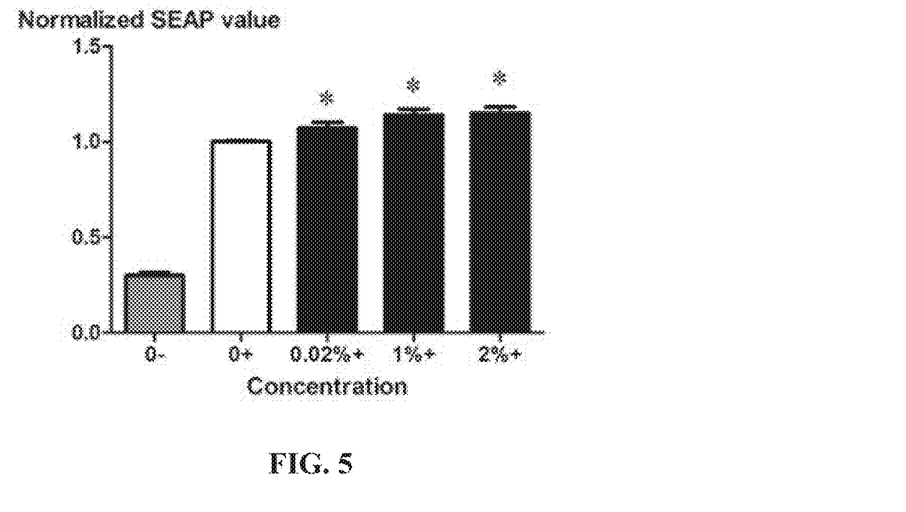
FIG. 5 shows the activity of SEAP after exposure to different concentrations of water samples. In this case, 0− and 0+ were the control group, 0− showed untransfected Hela cells that were not exposed; 0+ indicates transfected Hela cells that were not exposed; 0.02%+ represents the experimental group having the transfected Hela cells with 0.02% concentration of water samples.

As can be seen from FIG. 5, there was a significant difference between the different exposure groups and the control group (p<0.05). The exposure group with a water sample concentration of 0.02% concentration demonstrates a significant difference from the control group, which indicates that the cell lines constructed by the method can characterize early cell damage, and the results show a dose-effect relationship.

Comparative Example 1

Cytotoxicity Test—Cell Proliferation Inhibition Rate CCK-8 Test

Step 1, in a 96-well plate, Hela cells were seeded at a density of 10,000 cell/well;

Step 2, after the cells were cultured for 24 h, arsenic dilutions with concentrations of 0, 0.5, 1, 2, and 5 μmol/L were used as toxic substrates and the Hela cells were exposed to the arsenic dilutions for 24 h;

Step 3, 10 μL of CCK-8 reagent was added to each well. After incubating the 96-well plate for 1-4 h, the OD value of each well at 450 nm was measured with a microplate reader.

Figure 2:
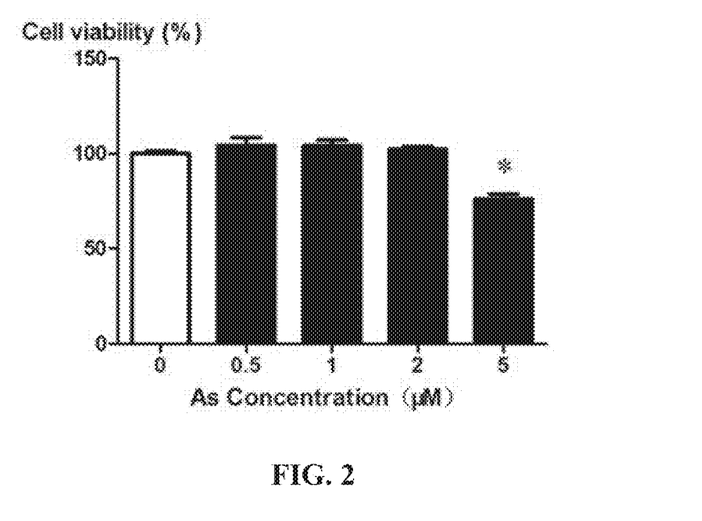
FIG. 2 shows the cell viability after exposure to different concentrations of arsenic (μmol/L) in Comparative Example 1.

As shown in FIG. 2, the results of Comparative Example 1 show that an arsenic concentration of 0-2 μmol/L do not cause significant cell proliferation inhibition, and an arsenic concentration of 5 μmol/L causes significant proliferation inhibition.

Comparative Example 2

Cytotoxicity Test—Intracellular ROS Test

Step 1, in a 96-well plate, Hela cells were seeded at a density of 10,000 cell/well;

Step 2, after the cells were cultured for 24 h, arsenic dilutions with concentrations of 0, 0.5, 1, 2, and 5 μmol/L were used as toxic substrates and the Hela cells were exposed to the arsenic dilutions for 24 h;

Step 3, the medium was aspirated and the cells were washed with Hanks buffer. The DCF probe and Hoechst 33342 probe were diluted to 10 μmol/L and 2.5 μg/mL with Hanks buffer, 100 μL of diluted probe was added to each well. After incubating the 96-well plate for 20 min, each well was washed with Hanks buffer and the fluorescence at 488/530 nm and 350/460 nm was measured using a microplate reader.

Figure 3:
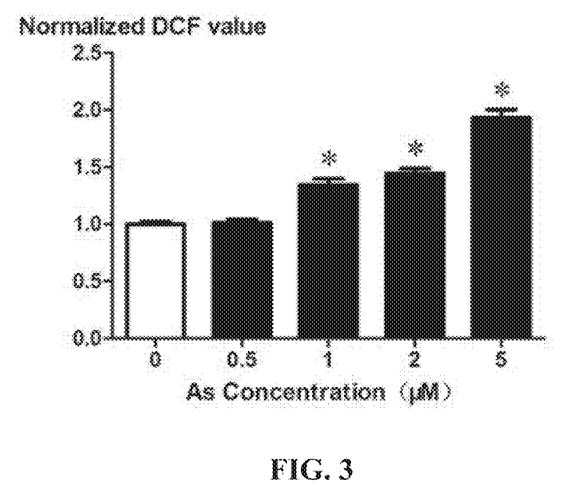
FIG. 3 shows the intracellular reactive oxygen species (ROS) level after exposure to different concentrations of arsenic (μmol/L) in Comparative Example 2.

As shown in FIG. 3, the detection result of Comparative Example 2 shows that an arsenic concentration of between 0 to 0.5 μmol/L does not cause significant increase of intracellular ROS levels, and a significant increase of intracellular ROS level is shown when the arsenic concentration reaches 1 μmol/L which indicates the oxidative stress.

Comparative Example 3

Cytotoxicity Test—Mitochondrial Membrane Potential JC-1 Detection

Step 1, in a 96-well plate, Hela cells were seeded at a density of 10,000 cell/well;

Step 2, after the cells were cultured for 24 h, arsenic dilutions with concentrations of 0, 0.5, 1, 2, and 5 μmol/L were used as toxic substrates and the Hela cells were exposed to the arsenic dilutions for 24 h;

Step 3, 10× incubation fluid was diluted into 1× incubation solution with ddH$_2$O, 1 μL of JC-1 was added to each 500 μL of 1× incubation solution, and the mixture was mixed with vortex to obtain JC-1 working solution, after centrifugation at 10,000 rpm for 1 min, the supernatant was taken;

Step 4, the medium was aspirated and the cells were washed with Hanks buffer. 100 μL of JC-1 working solution was added to each well. After incubation for 20 min, the fluorescence values at 488/530 nm and 530/590 nm were measured by a microplate reader.

Figure 4:
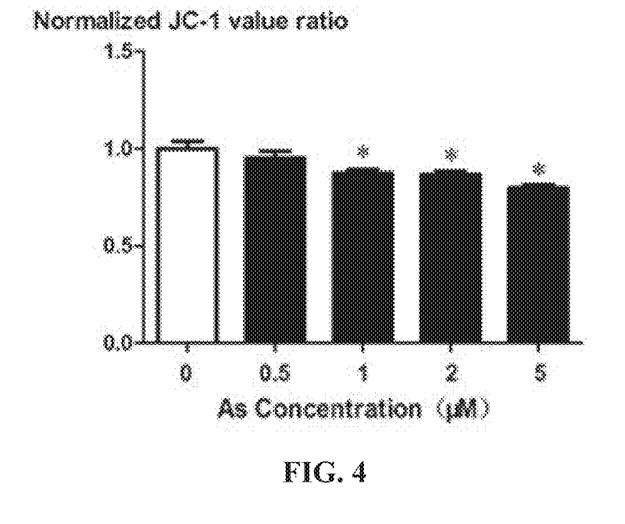
FIG. 4 shows the mitochondrial membrane potential changes after exposure to different concentrations of arsenic (μmol/L) in Comparative Example 3.

As shown in FIG. 4, the results of Comparative Example 3 show that arsenic at a concentration from 0 to 0.5 μmol/L does not cause significant changes in mitochondrial membrane potential, and a significant mitochondrial membrane potential change occurred when the arsenic concentration is 1 μmol/L which characterizes early cell apoptosis.

Comparative Example 4

Cytotoxicity Test—Cell Proliferation Inhibition Rate CCK-8 Test

Step 1, in a 96-well plate, Hela cells were seeded at a density of 10,000 cell/well;

Step 2, after the cells were cultured for 24 h, water sample dilutions with concentrations of 0, 0.02%, 0.2%, 1%, and 2% were used as toxic substrates and the Hela cells were exposed to the water sample dilutions for 24 h;

Step 3, 10 μL of CCK-8 reagent was added to each well. After incubating the 96-well plate for 1-4 h, the OD value of each well at 450 nm was measured with a microplate reader.

Figure 6:
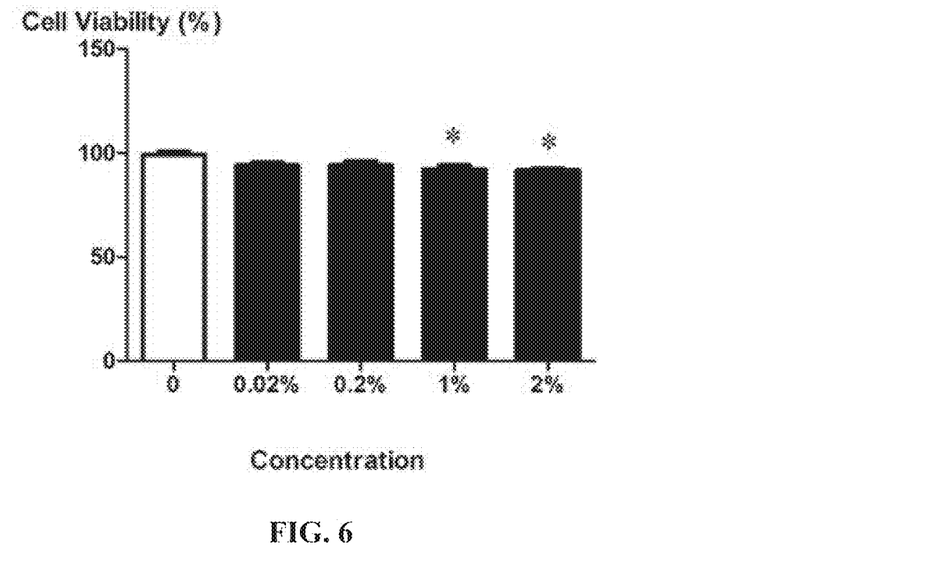
FIG. 6 shows the cell viability after exposure to different concentrations of water samples in Comparative Example 4.

As shown in FIG. 6, the results of Comparative Example 4 show that the water samples do not cause significant cell proliferation inhibition at the concentration of 0 to 0.2%, and significant proliferation inhibition occurred at the water sample concentration of 1%.

Comparative Example 5

Cytotoxicity Test—Intracellular ROS Test

Step 1, in a 96-well plate, Hela cells were seeded at a density of 10,000 cell/well;

Step 2, after the cells were cultured for 24 h, water sample dilutions with concentrations of 0, 0.02%, 0.2%, 1%, and 2% were used as toxic substrates and the Hela cells were exposed to the water sample dilutions for 24 h;

Step 3, the medium was aspirated and the cells were washed with Hanks buffer. The DCF probe and Hoechst 33342 probe were diluted to 10 μmol/L and 2.5 μg/mL with Hanks buffer, 100 μL of diluted probe was added to each well. After incubating the 96-well plate for 20 min, each well plate was washed with Hanks buffer and the fluorescence at 488/530 nm and 350/460 nm were respectively measured using a microplate reader.

Figure 7:
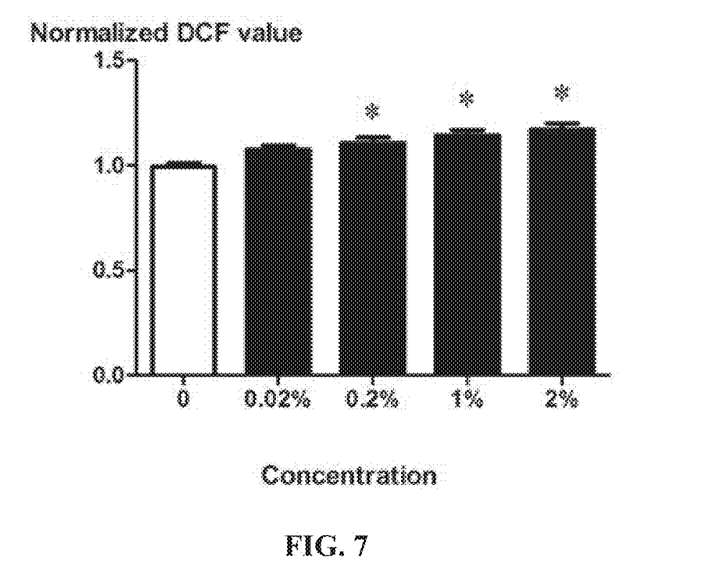
FIG. 7 shows the intracellular reactive oxygen species (ROS) level of the cell after exposure to different concentrations of water samples in Comparative Example 5.

As shown in FIG. 7, the detection result of Comparative Example 5 shows that the water samples do not cause significant intracellular ROS levels at concentrations of 0 to 0.02%, and a significant increase of intracellular ROS level occurs at the water sample concentration of 0.2% which indicates the existence of oxidative stress.

Comparative Example 6

Cytotoxicity Test—Mitochondrial Membrane Potential JC-1 Detection

Step 1, in a 96-well plate, Hela cells were seeded at a density of 10,000 cell/well;

Step 2, after the cells were cultured for 24 h, water sample dilutions with concentrations of 0, 0.02%, 0.2%, 1%, and 2% were used as toxic substrates and the Hela cells were exposed to the water sample dilutions for 24 h;

Step 3, 10× incubation fluid was diluted into 1× incubation solution with ddH$_2$O, 1 μL of JC-1 was added to each 500 μL of 1× incubation solution, and the mixture was mixed with vortex to obtain JC-1 working solution. After centrifugation at 10,000 rpm for 1 min, the supernatant was taken;

Step 4, the medium was aspirated and the cells were washed with Hanks buffer. 100 μL of JC-1 working solution was added to each well. After incubation for 20 min, the fluorescence values at 488/530 nm and 530/590 nm of each well were measured by a microplate reader.

Figure 8:
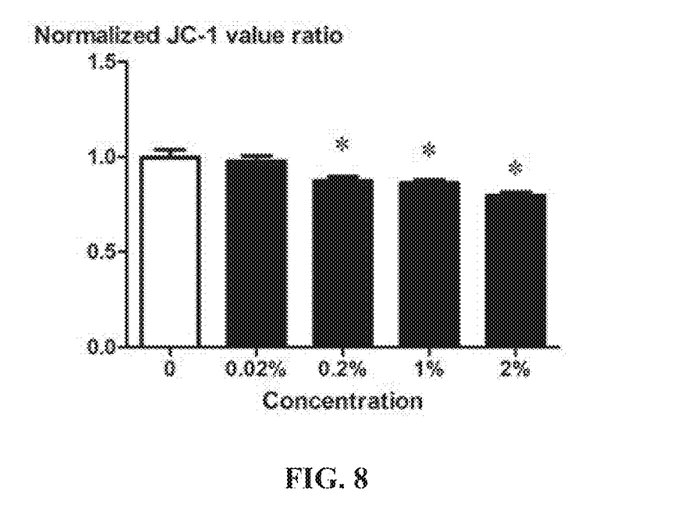
FIG. 8 shows the change in mitochondrial membrane potential of cells after exposure to different concentrations of water samples in Comparative Example 6.

As shown in FIG. 8, the results of Comparative Example 6 show that the water samples did not cause significant changes in mitochondrial membrane potential at a concentration of 0 to 0.02%, and a significant mitochondrial membrane potential change occurs at a water sample concentration of 0.2% which characterizes early cell apoptosis.

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for constructing a reporter gene cell line and measuring sensitivity of the reporter gene cell line to a poisonous pollutant, the method comprising:
    ligating a CHOP promoter and a secreted embryonic alkaline phosphatase (SEAP) gene in a lentiviral plasmid to construct a lentiviral CHOP-SEAP plasmid vector;
    transfecting the lentiviral CHOP-SEAP plasmid vector into Hela cells to construct a reporter gene cell line comprising transfected Hela cells;
    using arsenic as a poisonous pollutant, diluting the arsenic to obtain arsenic dilutions having concentrations of 0, 0.05, 0.1, 0.15, 0.2, 0.5, and 1 mol/L;
    exposing the arsenic dilutions to the transfected Hela cells for 24 hours to obtain treated Hela cells;
    incubating culture supernatants of the treated Hela cells at 65° C. for 30 minutes; and
    detecting a SEAP activity of the culture supernatants of the treated Hela cells by a SEAP Reporter Gene Assay kit comprising a cell-based alkaline phosphatase standard and a SEAP substrate;
    wherein:
    detecting the SEAP activity comprises diluting the cell-based alkaline phosphatase standard to obtain standard dilutions; adding the standard dilutions and the culture supernatants of the treated Hela cells to a 96-well white plate and adding the SEAP substrate to each well; and incubating the 96-well white plate at room temperature for 10-30 minutes and detecting the chemiluminescence of the standard dilutions and the culture supernatants of the treated Hela cells.

2. A method for detecting water toxicity, comprising:
    ligating a CHOP promoter and a secreted embryonic alkaline phosphatase (SEAP) gene in a lentiviral plasmid to construct a lentiviral CHOP-SEAP plasmid vector;
    transfecting the lentiviral CHOP-SEAP plasmid vector into Hela cells to construct a reporter gene cell line comprising transfected Hela cells;
    concentrating 5 L water samples by solid phase extraction and then diluting with 2% DMSO to 1 mL to obtain concentrated water samples; diluting the concentrated water samples to four dilutions respectively comprising by volume 0, 0.02%, 1%, and 2% of the concentrated water samples;
    performing parallel comparison tests and exposing the transfected Hela cells to the four dilutions for 24 hours to obtain treated Hela cells;
    incubating culture supernatants of the treated Hela cells at 65° C. for 30 minutes; and
    detecting a SEAP activity of the culture supernatants of the treated Hela cells by a SEAP Reporter Gene Assay kit;
    wherein:
    detecting the SEAP activity comprises diluting the cell-based alkaline phosphatase standard to obtain standard dilutions; adding the standard dilutions and the culture supernatants of the treated Hela cells to a 96-well white plate and adding the SEAP substrate to each well; and incubating the 96-well white plate at room temperature for 10-30 minutes and detecting the chemiluminescence of the standard dilutions and the culture supernatants of the treated Hela cells.

3. A method for constructing a reporter gene cell line, the method comprising:
    1) cleaving pHBLV-CMVIE-ZsGreen-Puro vector with EcoRI and XhoI enzymes, and extracting cleaved vector by gel electrophoresis;
    2) amplifying a secreted embryonic alkaline phosphatase (SEAP) gene and a CHOP promoter by PCR to obtain a SEAP fragment and a CHOP promoter fragment;
    3) ligating the SEAP fragment and the CHOP promoter fragment of 2) to the cleaved vector of 1) to obtain a CHOP-SEAP lentiviral plasmid vector;
    4) transforming the CHOP-SEAP lentiviral plasmid vector of 3) into DH5a competent cells, cultivating the DH5a competent cells and selecting positive clones by PCR identification;
    5) extracting the CHOP-SEAP lentiviral plasmid vector from the positive clones of 4);
    6) transfecting the CHOP-SEAP lentiviral plasmid vector of 5) to 293T cells, cultivating the 293T cells, and collecting the CHOP-SEAP lentiviral plasmid vector from culture supernatants;
    7) transfecting the CHOP-SEAP lentiviral plasmid vector of 6) to Hela cells to obtain transfected Hela cells; and
    8) isolating a reporter gene cell line from the transfected Hela cells of 7) through screening for puromycin resistance.

4. A method for measuring sensitivity of the reporter gene cell line of claim 3 to a poisonous pollutant, the method comprising:
    using arsenic as a poisonous pollutant, diluting the arsenic to obtain arsenic dilutions having concentrations of 0, 0.05, 0.1, 0.15, 0.2, 0.5, and 1 mol/L;
    exposing the arsenic dilutions to Hela cells of the reporter gene cell line for 24 hours to obtain treated Hela cells;
    incubating culture supernatants of the treated Hela cells at 65° C. for 30 minutes; and
    detecting a SEAP activity of the culture supernatants of the treated Hela cells by a SEAP Reporter Gene Assay kit comprising a cell-based alkaline phosphatase standard and a SEAP substrate;
    wherein:
    detecting the SEAP activity comprises diluting the cell-based alkaline phosphatase standard to obtain standard dilutions; adding the standard dilutions and the culture supernatants of the treated Hela cells to a 96-well white plate and adding the SEAP substrate to each well; and incubating the 96-well white plate at room temperature for 10-30 minutes and detecting the chemiluminescence of the standard dilutions and the culture supernatants of the treated Hela cells.

5. A method for detecting water toxicity using the reporter gene cell line of claim 3, the method comprising:
concentrating 5 L water samples by solid phase extraction and then diluting with 2% DMSO to 1 mL to obtain concentrated water samples;
diluting the concentrated water samples to four dilutions respectively comprising by volume 0, 0.02%, 1%, and 2% of the concentrated water samples;
performing parallel comparison tests and exposing Hela cells of the reporter gene cell line to the four dilutions for 24 hours to obtain treated Hela cells;
incubating culture supernatants of the treated Hela cells at 65° C. for 30 minutes; and
detecting a SEAP activity of the culture supernatants of the treated Hela cells by a SEAP Reporter Gene Assay kit,
wherein:
detecting the SEAP activity comprises diluting the cell-based alkaline phosphatase standard to obtain standard dilutions; adding the standard dilutions and the culture supernatants of the treated Hela cells to a 96-well white plate and adding the SEAP substrate to each well; and incubating the 96-well white plate at room temperature for 10-30 minutes and detecting the chemiluminescence of the standard dilutions and the culture supernatants of the treated Hela cells.

* * * * *